US007615348B2

(12) United States Patent
Crothers et al.

(10) Patent No.: US 7,615,348 B2
(45) Date of Patent: Nov. 10, 2009

(54) ELECTROCHEMICAL METHOD TO MEASURE DNA ATTACHMENT TO AN ELECTRODE SURFACE IN THE PRESENCE OF MOLECULAR OXYGEN

(75) Inventors: Donald M. Crothers, Northford, CT (US); R. Erik Holmlin, San Diego, CA (US); Honghua Zhang, San Diego, CA (US); Chunnian Shi, San Diego, CA (US)

(73) Assignee: Genohm Sciences, San Diego, CA (US)

( * ) Notice: Subject to any disclaimer, the term of this patent is extended or adjusted under 35 U.S.C. 154(b) by 0 days.

(21) Appl. No.: 11/836,046

(22) Filed: Aug. 8, 2007

(65) Prior Publication Data
US 2008/0026397 A1 Jan. 31, 2008

Related U.S. Application Data

(60) Division of application No. 10/429,291, filed on May 2, 2003, now Pat. No. 7,258,978, and a continuation-in-part of application No. 10/424,542, filed on Apr. 24, 2003, now abandoned.

(60) Provisional application No. 60/424,656, filed on Nov. 6, 2002.

(51) Int. Cl.
*C12Q 1/68* (2006.01)
*C12Q 1/70* (2006.01)
*C12P 19/34* (2006.01)
*C07H 21/00* (2006.01)

(52) U.S. Cl. .............................. 435/6; 435/5; 435/91.1; 435/91.2; 536/23.1; 536/24.3; 536/26.6

(58) Field of Classification Search ..................... 435/5, 435/6, 91.1, 91.2; 536/23.1, 24.3, 26.6
See application file for complete search history.

(56) References Cited

U.S. PATENT DOCUMENTS

| 4,840,893 | A  | * | 6/1989  | Hill et al.     | ........ 435/6   |
|-----------|----|---|---------|-----------------|-----------------|
| 6,180,346 | B1 |   | 1/2001  | Thorp et al.    |                 |
| 6,316,607 | B1 | * | 11/2001 | Massey et al.   | ........ 536/22.1 |
| 7,258,978 | B2 | * | 8/2007  | Crothers et al. | ........ 435/6   |
| 2003/0152960 | A1 | * | 8/2003 | Thorp et al.    | ........ 435/6   |

(Continued)

FOREIGN PATENT DOCUMENTS

WO    WO 02/083839 A2    10/2002

OTHER PUBLICATIONS

Steel et al. Analytical Chemistry, vol. 70, No. 22, 1998, pp. 4670-4677.*

*Primary Examiner*—Jezia Riley
(74) *Attorney, Agent, or Firm*—Knobbe Martens Olson & Bear LLP

(57) ABSTRACT

The present disclosure provides methods and compositions for conducting an assay to detect a polynucleotide. In particular, ruthenium complexes having reduction potentials that do not coincide with the reduction potential of molecular oxygen are disclosed and amperometric techniques for their use are described. In preferred embodiments, the ruthenium complex is ruthenium (III) pentaamine pyridine and the polynucleotide that is detected is DNA. Further, techniques for enhancing detectable contrast between hybridized and unhybridized nucleic acids are disclosed. In particular, the use of elongated target strands as well as the use of uncharged probe strands are discussed.

24 Claims, 1 Drawing Sheet

U.S. PATENT DOCUMENTS

| | | |
|---|---|---|
| 2004/0086892 A1 | 5/2004 | Crothers et al. |
| 2004/0086894 A1 | 5/2004 | Crothers et al. |
| 2004/0086895 A1 | 5/2004 | Crothers et al. |
| 2005/0118616 A1 | 6/2005 | Kawashima et al. |
| 2005/0176035 A1 | 8/2005 | Crothers |
| 2005/0186590 A1 | 8/2005 | Crothers et al. |

* cited by examiner

ELECTROCHEMICAL METHOD TO MEASURE DNA ATTACHMENT TO AN ELECTRODE SURFACE IN THE PRESENCE OF MOLECULAR OXYGEN

RELATED APPLICATIONS

This application is a divisional of U.S. patent application Ser. No. 10/429,291 entitled "ELECTROCHEMICAL METHOD TO MEASURE DNA ATTACHMENT TO AN ELECTRODE SURFACE IN THE PRESENCE OF MOLECULAR OXYGEN," filed May 2, 2003, which itself claims priority from U.S. Pat. Application No. 60/424,656 entitled UNIVERSAL TAG ASSAY filed Nov. 6, 2002, and also claims priority from, and is a continuation-in-part application of U.S. patent application Ser. No. 10/424,542 entitled "UNIVERSAL TAG ASSAY," filed Apr. 24, 2003. The subject matter of the aforementioned applications is hereby incorporated by reference in its entirety.

BACKGROUND OF THE INVENTION

1. Field of the Invention

This invention relates to a method of detecting nucleic acid hybridization in an electrochemical assay. More particularly, the invention relates to such a method of detecting nucleic acid hybridization in the presence of molecular oxygen. Preferred embodiments include the use of ruthenium amperometry to detect hybridization of DNA or RNA molecules to detection probes immobilized on a detector, preferably a universal chip having gold or carbon electrodes.

2. Description of the Related Art

One method to detect nucleic acid hybridization is to detect a quantity of counterions surrounding the nucleic acid. Accordingly, hybridized nucleic acid would tend to be surrounded by more of the counterions than would single stranded nucleic acid. The counterions are typically detected by an electrochemical reaction, for example by reduction of a trivalent ion to divalent; in this way, the counterions function as an electron transfer species.

Electrochemical quantitation is described in A. B. Steel et al., *Electrochemical Quantitation of DNA Immobilized on Gold*, Anal. Chem. 70:4670-77 (1998), hereby expressly incorporated by reference in its entirety. In this publication, Steel et al. describe the use of cobalt (III) trisbipyridyl and ruthenium (III) hexaamine as species which interact with surface-immobilized DNA.

The complex $Ru(NH_3)_6^{3+}$ has a reduction potential on a gold electrode of approximately −250 mV versus Ag/AgCl reference. This potential overlaps with the potential range at which diatomic oxygen ($O_2$) is reduced on a gold electrode at neutral pH. If oxygen is present during an assay using $Ru(NH_3)_6^{3+}$, reduction of the oxygen causes a background signal that interferes with the interpretation of the current associated with the reduction of $Ru(NH_3)_6^{3+}$.

One technique used to diminish oxygen's effect is to remove the oxygen in close proximity to the electrochemical cell that would be present in ordinary laboratory conditions. This can be achieved by deaeration with another gas, such as nitrogen or argon. The inert gas is typically administered from a tank to the electrochemical cell before and during the assay to minimize the amount of oxygen present. However, because of the additional steps and equipment involved, deaeration procedures are generally inconvenient, time-consuming, and expensive.

Accordingly, there exists an unmet need in the art for a method of accurately detecting DNA hybridization despite the presence of molecular oxygen in the assay environment.

SUMMARY OF THE INVENTION

One aspect of the present invention is a method of detecting polynucleotide hybridization, including: providing a probe polynucleotide immobilized to an electrode; contacting the probe with a sample potentially containing target polynucleotide capable of hybridizing with the probe; contacting the probe and any target hybridized thereto with a moiety having a reduction potential that is substantially different from the reduction potential of diatomic oxygen; and electrochemically determining whether target has hybridized to the probe.

Another aspect of the present invention is a method of detecting polynucleotide hybridization, including: providing a probe polynucleotide immobilized to an electrode; contacting the probe with a sample potentially containing target polynucleotide capable of hybridizing with the probe; contacting the probe and any target hybridized thereto with a ruthenium complex having the formula:

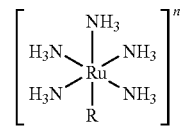

wherein R is an electron withdrawing ligand and n is an integer; and electrochemically determining whether target has hybridized to the probe.

Another aspect of the invention is a method for detecting a polynucleotide, including: immobilizing a target polynucleotide on an electrode; contacting the target polynucleotide with a ruthenium complex of the formula:

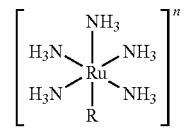

wherein R is an electron withdrawing ligand and n is an integer; and electrochemically detecting the ruthenium complex as an indicator of the presence of immobilized target polynucleotide.

Another aspect of the invention is a method for quantitating polynucleotide, including: binding polynucleotide to an electrode; contacting the polynucleotide with a ruthenium complex of the formula:

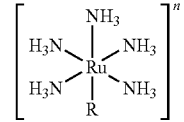

wherein R is an electron withdrawing ligand and n is an integer; and electrochemically detecting the quantity of ruthenium complex associated with the polynucleotide.

Another aspect of the invention is a method of detecting polynucleotide hybridization, including: providing a probe polynucleotide immobilized to an electrode; providing a target polynucleotide that is substantially longer than the probe polynucleotide and that is potentially capable of hybridizing with the probe polynucleotide; contacting the probe with the target polynucleotide; contacting the probe and any target hybridized thereto with a transition metal complex; and electrochemically determining whether the target has hybridized to the probe.

Another aspect of the invention is a method of detecting polynucleotide hybridization, including: providing a probe polynucleotide immobilized to an electrode; providing a target polynucleotide that is potentially capable of hybridizing with the probe polynucleotide; contacting the probe with the target polynucleotide; elongating any target polynucleotide that has hybridized to the probe; contacting any hybridized target polynucleotide with a transition metal complex; and electrochemically determining whether the target has hybridized to the probe.

Another aspect of the invention is a method of detecting polynucleotide hybridization, including: providing a nucleic acid analog probe immobilized to an electrode; providing a target polynucleotide that is potentially capable of hybridizing with the probe; contacting the probe with the target polynucleotide; contacting any hybridized target polynucleotide with a transition metal complex; and electrochemically determining whether the target has hybridized to the probe.

Another aspect of the invention is a kit for detecting a target polynucleotide, including: an assay device having a binding portion capable of binding target polynucleotide; and a counterion reagent able to associate with the target polynucleotide and having a reduction potential that is substantially different from the reduction potential of diatomic oxygen.

A further aspect of the invention is a method of detecting polynucleotide hybridization, including: providing a probe polynucleotide immobilized to a non-gold electrode; contacting the probe with a sample potentially containing target polynucleotide capable of hybridizing with the probe; contacting any hybridized target with a moiety having a reduction potential that is substantially different from the reduction potential of diatomic oxygen at the electrode; and electrochemically determining whether target has hybridized to the probe.

DETAILED DESCRIPTION OF THE PREFERRED EMBODIMENT

Figure 1:
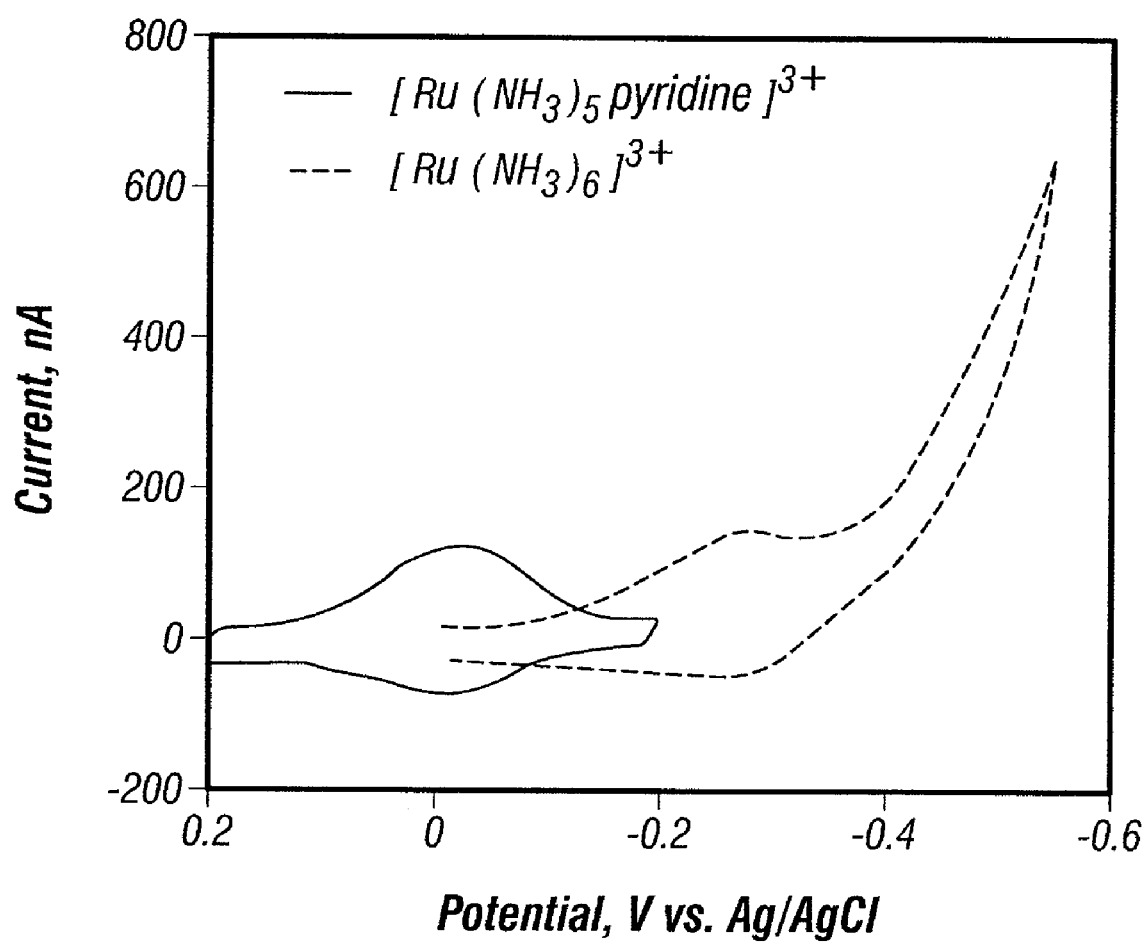
FIG. 1 shows a voltammogram comparing the reduction potentials of $Ru(NH_3)_5pyridine^{3+}$ and $Ru(NH_3)_6^{3+}$.

The present invention relates to methods of analyzing a nucleic acid. In preferred embodiments, the nucleic acid comprises DNA. Hence, references to "DNA" are not intended to imply that other nucleic acids or nucleic acid analogs (e.g., RNA, PNA) cannot be used in practicing the present invention, except as so required in the claims.

Ruthenium-based counterions are particularly advantageous in quantitating polynucleotides for the purpose of detecting hybridization. Ruthenium amperometry and the use of the complexes $Ru(NH_3)_6^{3+}$ and $Ru(NH_3)_5pyridine^{3+}$ for this purpose are disclosed in copending U.S. Pat. Application No. 60/424,656, filed Nov. 6, 2002; U.S. patent application Ser. No. 10/424,542 entitled "UNIVERSAL TAG ASSAY," filed Apr. 24, 2003, both of which are hereby incorporated by reference in their entirety.

It has been discovered that the ligands surrounding the ruthenium atom in various ruthenium complexes determine the reduction potential of the complex. It has further been discovered that if one or more of the six amine groups of ruthenium hexaamine is replaced with an electron withdrawing ligand such as pyridine, the reduction potential of the complex can shift in the positive direction and out of the oxygen reduction window. Use of such a complex greatly improves the measurement of hybridization by this method since the reaction can be performed in the presence of oxygen, eliminating the need for expensive and time-consuming deaeration procedures. Accordingly, some embodiments of the present invention include the use of a counterion having a reduction potential that does not overlap with that of molecular oxygen.

It has also been discovered that the use of electrodes other than gold electrodes can be advantageous for some assays. Electrodes that are not substantially made of gold are herein described as "non-gold" electrodes. Particularly preferred non-gold electrodes include carbon electrodes. For example, when using a carbon electrode instead of a gold electrode, $Ru(NH_3)_6^{3+}$ has a reduction potential that does not overlap with the reduction potential of diatomic oxygen. Accordingly, the use of a carbon electrode for an assay in which $Ru(NH_3)_6^{3+}$ is a counterion can offset the need to deaerate the assay environment. However, where gold electrodes are preferred to other electrodes, such as carbon electrodes, it is generally advantagous to use a species other than $Ru(NH_3)_6^{3+}$ as a counterion.

Ruthenium complexes featuring substituted ligands such as pyridine have previously been studied for other purposes. For example, the attachment of ruthenium pentaamine pyridine complexes to alkanethiols for the study of electron transfer kinetics in self assembled monolayers is described in H. O. Finklea et al., *Electron-Transfer Kinetics in Organized Thiol Monolayers with Attached Pentaammine(pyridine)ruthenium Redox Centers*, J. Am. Chem. Soc. 114:3173-3181 (1992) and in H. O. Finklea, *Self-assembled Monolayers on Electrodes*, Encyclopedia of Analytical Chemistry, John Wiley & Sons Ltd. (2000). The use of $Ru(NH_3)_5py^{3+,2+}$ complexes in electrochemical assays is also described in Hill et al. (U.S. Pat. No. 4,840,893). All of these references are hereby expressly incorporated by reference in their entirety.

Some embodiments of the present invention use a substituted ruthenium pentaamine complex as shown below.

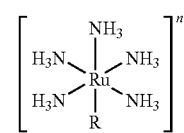

In this structure, R is an electron withdrawing ligand. In some embodiments, the electron withdrawing ligand is a heterocyclic moiety, preferably a nitrogen-containing heterocycle such as substituted or unsubstituted pyridine, pyrimidine, pyridazine, or pyrazine. Other ligands that are suitable for use in the present invention include phosphite derivatives and isonitrile derivatives.

In the structure above, n represents the electrical charge of the complex. Complexes according to the present invention typically carry a positive charge. In some preferred embodiments, the charge is 3+.

Further, some useful counterions include dimers or polymers in which one or more monomeric subunits contain one or more electron withdrawing ligands.

Table 1 depicts several types of ruthenium counterions that are suitable for use with the present invention. For the R group substituents that appear in some of these counterions, Table 1 lists some of the preferred moieties, though it will be appreciated by those of skill in the art that other substituted or unsubstituted alkyl, aryl, and/or heteroatom moieties can also be used.

TABLE 1

Structures of Various Ruthenium Complexes

| Complex | Ligand | Ligand Structure | Substituent |
|---|---|---|---|
| $Ru(NH_3)_5py^{3+}$ | Pyridine derivative | (pyridine with $R^1$–$R^5$) | $R^1$ through $R^5$ = —H, —$CH_3$, —$CO_2CH_3$, —I, —Cl, —Br, —$CH(OH)_2$, —$CH_2OH$, —$CONH_2$, —$CO_2$, —$CO_2CH_3$, —$CO_2H$, —CHO |
| $Ru(NH_3)_5pym^{3+}$ | Pyrimidine | ($C_4H_4N_2$, 1.3-Diazine) | |
| $Ru(NH_3)_5Pyd^{3+}$ | Pyridazine | ($C_4H_4N_2$, 1.2-Diazine) | |
| $Ru(NH_3)_5Pz^{3+}$ | Pyrazine | ($C_4H_4N_2$, 1.4-Diazine) | |
| $Ru(NH_3)_5Pi^{3+}$ | Phosphite derivative | $(R^1\!-\!O\!\!-\!\!)_3 P$ | $R^1$ = —H, —$CH_3$, —$CH_2CH_3$, —$C_6H_5OH$ |
| $Ru(NH_3)_5(CNR)^{3+}$ | Isonitrile derivative | $R^1$—$CH_2$—N≡C: | $R^1$ = —H, —$CH_3$, —$CH_2CH_3$, —$C_6H_5OH$ |
| $(NH_3)_5RuPzRu(NH_3)_5^{5+}$ | Pyrazine | ($C_4H_4N_2$, 1.4-Diazine) | |
| $(NH_3)_5RuPzRu(NH_3)_5^{6+}$ | Pyrazine | ($C_4H_4N_2$, 1.4-Diazine) | |
| $[(NH_3)_5Ru(PzRu(NH_3)_4)_nPzRu(NH_3)_5]^{+(3n+6)}$ | Rutheniumpentaamine Pyrazine | $PzRu(NH_3)_5^{3+}$ | |
| $[(NH_3)_5Ru(PzRu(NH_3)_4)_nPzRu(NH_3)_5]^{+(3n+4)}$ | Rutheniumpentaamine Pyrazine | $PzRu(NH_3)_5^{2+}$ | |
| $[—(CH_2CHPyRu(NH_3)_5)_n]^{+3n}$ | Polyvinyl pyridine | —($CH_2CHPy$)— | |

In some embodiments, counterions can contain more than one electron withdrawing ligand. Such additional ligands can be the same or similar to those indicated above. Further, counterions need not contain ruthenium; for example, other transition metal atoms can be used to create a complex capable of electron transfer. Other chemical moieties that are capable of transferring an electrical charge, preferably by a redox reaction, can also be used as counterions. However, it remains advantageous for a counterion to have a reduction potential that does not overlap with the reduction potential of diatomic oxygen.

The flow of current associated with the reduction of diatomic oxygen on a gold electrode begins to interfere with the assay at approximately −250 mV versus an Ag/AgCl reference. It is preferred that the reduction potential of a counterion used in connection with the present invention be positive of that value. Counterions having a reduction potential that is positive of −200 mV versus an Ag/AgCl reference are preferred. Those that are positive of −100 mV versus an Ag/AgCl reference are more preferred, and those that are approximately 0 mV or positive of 0 mV versus an Ag/AgCl reference are most preferred.

However, it can be advantageous not to use counterions having a reduction potential that is too positive. For example, a counterion that will oxidize water is generally not favorable for use in an aqueous medium. Accordingly, preferred counterions for use in an aqueous assay medium have a reduction potential that is negative of +1.0 V versus an Ag/AgCl reference. More preferably, the reduction potential is negative of +500 mV versus an Ag/AgCl reference. For example, the complex ruthenium(III) pentaamine pyridine has reduction potential that is approximately 0 mV versus an Ag/AgCl reference, and is a particularly preferred counterion.

In some embodiments, the invention uses the metal complex ruthenium(III) pentaamine pyridine ($Ru(NH_3)_5py^{3+}$ shown below), for detecting DNA hybridization at an electrode surface.

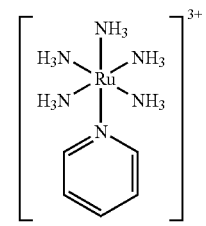

Because of its trivalency, this molecule can associate avidly to negatively charged phosphodiesters of a DNA backbone. In preferred embodiments, the DNA is attached to an electrode to conduct an electrochemical assay. Applying a reducing potential to the electrode causes reduction of the ruthenium. In the case of $Ru(NH_3)_5py^{3+}$, the reduction is typically from the trivalent ion to divalent. This reduction of $Ru(NH_3)_5py^{3+}$ is not convolved with the reduction of oxygen, as is often a problem when using $Ru(NH_3)_6^{3+}$.

The quantity of counterions bound to the DNA can be calculated from the number of electrons transferred during the reduction. The following equation can be used to calculate the amount of DNA present based on a measured amount of a redox marker, such as in the electrochemical detection of a ruthenium species:

$$\Gamma_{DNA} = \Gamma_0 (z/m)(N_A)$$

In this equation, $\Gamma_{DNA}$ is the DNA surface density in molecules/cm², $\Gamma_0$ is the surface density of adsorbed redox marker (mol/cm²), m is the number of bases in the DNA probe, z is the charge of the redox species, and $N_A$ is Avogadro's constant.

FIG. 1 illustrates the separate electrochemical responses for $Ru(NH_3)_5py^{3+}$ and $Ru(NH_3)_6^{3+}$ bound to DNA films on gold electrodes in the presence of oxygen. As shown, the reduction potential of $Ru(NH_3)_5py^{3+}$ is approximately 0 mV, while that of $Ru(NH_3)_6^{3+}$ is approximately −250 to −300 mV.

Accordingly, one advantage of using a species such as $Ru(NH_3)_5py^{3+}$ is that its reduction potential of approximately 0 mV vs. Ag/AgCl is about 300 mV positive of where diatomic oxygen is reduced at a gold electrode. Using $Ru(NH_3)_5py^{3+}$ as a counterion allows a more accurate calculation of the amount of ruthenium (and a more accurate calculation of the amount of nucleic acid) based on the measured current. Measurements of nucleic acid hybridization at an electrode surface may thus be performed in aerated solutions without having to first remove dissolved molecular oxygen.

As indicated above, preferred embodiments of the present invention feature the use of a ruthenium complex in conducting an electrochemical assay. Preferably, such an assay detects nucleic acid hybridization using the general technique of Steele et al. (1998, Anal. Chem. 70:4670-4677), herein incorporated by reference.

Typically, in carrying out this technique, a plurality of nucleic acid probes which are complementary to a sequence of interest are used. Preferably, these probe strands are immobilized on a surface such as an electrode in contact with a liquid medium. Preferably, the surface is a gold electrode that is coated with a protein layer such as avidin to facilitate the attachment of the nucleic acid probe strands to the electrode. This protein layer should be porous, such that it allows ions to pass from the liquid medium to the electrode and vice versa. Alternatively, probe strands can be attached directly to the surface, for example by using a thiol linkage to covalently bind nucleic acid to a gold electrode.

Next, a target strand (a nucleic acid sample to be interrogated relative to the probe) can be contacted with the probe in any suitable manner known to those skilled in the art. For example, a plurality of target strands can be introduced to the liquid medium and allowed to intermingle with the immobilized probes. Preferably, the number of target strands exceeds the number of probe strands in order to maximize the opportunity of each probe strand to interact with target strands and participate in hybridization. If a target strand is complementary to a probe strand, hybridization can take place. Whether or not hybridization occurs can be influenced by various "stringency" factors such as temperature, pH, or the presence of a species able to denature various hybridized strands. Accordingly, it is often desirable to adjust the assay conditions to achieve a suitable level of stringency; maximum stringency would be a condition in which perfectly complementary strands may hybridize, while all other strands do not. Ideal conditions will generally be those which strike a balance between minimizing the number of hybridizations between noncomplementary strands (false positives) and minimizing the number of probes which remain unhybridized despite the presence of eligible complementary target strands (false negatives). Increasing the quantity and/or size of target strands are examples of techniques that can be useful in minimizing false negatives.

Counterions, such as $Ru(NH_3)_5py^{3+}$ can be introduced to the liquid medium and will tend to cloud around the negatively charged backbones of the various nucleic acid strands. Generally, the counterions will accumulate electrostatically around the phosphate groups of the nucleic acids whether they are single or double stranded. However, because a probe and target together physically constitute a larger amount of DNA than the probe alone, a double stranded DNA will have more counterions surrounding it. Although $Ru(NH_3)_5py^{3+}$ is a preferred counterion, any other suitable transition metal complexes or other counterions that associate with nucleic acid electrostatically and whose reduction or oxidation is electrochemically detectable in an appropriate voltage regime can be used.

Various techniques for measuring the amount of counterions can be used. In a preferred embodiment, amperometry is used to detect an electrochemical reaction at the electrode. Generally, an electrical potential will be applied to the electrode. As the counterions undergo an electrochemical reaction, for example, the reduction of a trivalent ion to divalent at the electrode surface, a measurable current is generated. The amount of current corresponds to the amount of counterions present, which in turn corresponds to the amount of negatively-charged phosphate groups on nucleic acids. Accordingly, measuring the current allows a quantitation of phosphate groups and can allow the operator to distinguish hybridized nucleic acid from unhybridized nucleic acid and determine whether the target being interrogated is complementary to the probe (and contains the sequence of interest).

Alternatively, the measurable distinction between single stranded and double stranded oligonucleotides can be made even more profound. One method is to use target strands which are substantially longer than the probe strands. Accordingly, the longer target strands will accumulate substantially more counterions which will be detectable if the target is hybridized to a probe. A preferred technique for elongating the target strands is rolling circle amplification (RCA). Longer target strands can be made and then introduced to the liquid medium surrounding the probes. Alternatively, it is possible to increase the length of a target strand after the strand has hybridized to a probe strand. This second technique is often referred to as "on-chip" amplification. Preferred methods of on-chip amplification are head-to-tail polymerization and RCA. On-chip amplification is discussed in greater detail in U.S. patent application Ser. No. 10/429,293 entitled "METHOD OF ELECTROCHEMICAL DETECTION OF SOMATIC CELL MUTATIONS," filed on May 2, 2003, which is hereby expressly incorporated by reference.

Another technique for increasing the signal contrast between single stranded and double stranded DNA is to limit the electrical signal from the probe strands. In particular, this can be done by limiting the electrical attraction between the probe strand and the counterions which participate in electron transfer. For example, if the probe strands are constructed such that they do not contain a negatively charged backbone, then they will not attract counterions. Accordingly, more of the detectable signal will be due to counterions associated with the target strands. In cases where hybridization has not occurred, the detectable signal will be measurably lower since the target strands are not present to participate in counterion attraction.

Probe strands without a negatively charged backbone can include peptide nucleic acids (PNAs), phosphotriesters, methylphosphonates. These nucleic acid analogs are known in the art.

In particular, PNAs are discussed in: Nielsen, "DNA analogues with nonphosphodiester backbones," *Annu Rev Biophys Biomol Struct,* 1995; 24:167-83; Nielsen et al., "An introduction to peptide nucleic acid," *Curr Issues Mol Biol,* 1999; 1(1-2):89-104; and Ray et al., "Peptide nucleic acid (PNA): its medical and biotechnical applications and promise for the future," *FASEB J.*, 2000 June; 14(9):1041-60; all of which are hereby expressly incorporated by reference in their entirety.

Phophotriesters are discussed in: Sung et al., "Synthesis of the human insulin gene. Part II. Further improvements in the modified phosphotriester method and the synthesis of seventeen deoxyribooligonucleotide fragments constituting human insulin chains B and mini-cDNA," *Nucleic Acids Res*, 1979 Dec. 20; 7(8):2199-212; van Boom et al., "Synthesis of oligonucleotides with sequences identical with or analogous to the 3'-end of 16S ribosomal RNA of *Escherichia coli*: preparation of m-6-2-A-C-C-U-C-C and A-C-C-U-C-m-4-2C via phosphotriester intermediates," *Nucleic Acids Res*, 1977 March; 4(3):747-59; and Marcus-Sekura et al., "Comparative inhibition of chloramphenicol acetyltransferase gene expression by antisense oligonucleotide analogues having alkyl phosphotriester, methylphosphonate and phosphorothioate linkages," *Nucleic Acids Res*, 1987 Jul. 24; 15(14):5749-63; all of which are hereby expressly incorporated by reference in their entirety.

Methylphosphonates are discussed in: U.S. Pat. No. 4,469,863 (Ts'o et al.); Lin et al., "Use of EDTA derivatization to characterize interactions between oligodeoxyribonucleoside methylphosphonates and nucleic acids," *Biochemistry*, 1989, Feb. 7; 28(3):1054-61; Vyazovkina et al., "Synthesis of specific diastereomers of a DNA methylphosphonate heptamer, d(CpCpApApApCpA), and stability of base pairing with the normal DNA octamer d(TPGPTPTPTPGPGPC)," *Nucleic Acids Res*, 1994 Jun. 25; 22(12):2404-9; Le Bec et al., "Stereospecific Grignard-Activated Solid Phase Synthesis of DNA Methylphosphonate Dimers," *J Org Chem*, 1996 Jan. 26; 61(2):510-513; Vyazovkina et al., "Synthesis of specific diastereomers of a DNA methylphosphonate heptamer, d(CpCpApApApCpA), and stability of base pairing with the normal DNA octamer d(TPGPTPTPTPGPGPC)," *Nucleic Acids Res*, 1994 Jun. 25; 22(12):2404-9; Kibler-Herzog et al., "Duplex stabilities of phosphorothioate, methylphosphonate, and RNA analogs of two DNA 14-mers," *Nucleic Acids Res*, 1991 Jun. 11; 19(11):2979-86; Disney et al., "Targeting a *Pneumocystis carinii* group I intron with methylphosphonate oligonucleotides: backbone charge is not required for binding or reactivity," *Biochemistry*, 2000 Jun. 13; 39(23):6991-7000; Ferguson et al, "Application of free-energy decomposition to determine the relative stability of R and S oligodeoxyribonucleotide methylphosphonates," *Antisense Res Dev*, 1991 Fall; 1(3):243-54; Thiviyanathan et al., "Structure of hybrid backbone methylphosphonate DNA heteroduplexes: effect of R and S stereochemistry," *Biochemistry*, 2002 Jan. 22; 41(3):827-38; Reynolds et al., "Synthesis and thermodynamics of oligonucleotides containing chirally pure R(P) methylphosphonate linkages," *Nucleic Acids Res*, 1996 Nov. 15; 24(22):4584-91; Hardwidge et al., "Charge neutralization and DNA bending by the *Escherichia coli* catabolite activator protein," *Nucleic Acids Res*, 2002 May 1; 30(9):1879-85; and Okonogi et al., "Phosphate backbone neutralization increases duplex DNA flexibility: A model for protein binding," *PNAS U.S.A.*, 2002 Apr. 2; 99(7):4156-60; all of which are hereby incorporated by reference.

In general, an appropriate nucleic acid analog probe will not contribute, or will contribute less substantially, to the attraction of counterions compared to a probe made of natural DNA. Meanwhile, the target strand will ordinarily feature a natural phosphate backbone having negatively charged groups which attract positive ions and make the strand detectable.

Alternatively, a probe may be constructed that contains both charged nucleic acids and uncharged nucleic acid analogs. Similarly, pure DNA probes can be used alongside probes containing uncharged analogs in an assay. However, precision in distinguishing between single stranded and double stranded will generally increase according to the electrical charge contrast between the probe and the target strands. Hence, the exclusive use of probes made entirely of an uncharged nucleic analog will generally allow the greatest signal contrast between hybridized and non-hybridized molecules on the chip. In general, probe strands containing methylphosphonates are preferred. Strands containing phosphotriesters are less preferred since they are generally not soluble in an aqueous medium.

Although techniques (such as those above) for enhancing the measurable distinction between single stranded and double stranded oligonucleotides can be advantageously used in connection with a redox-based assay employing a counterion capable of reaction at a potential outside the oxygen reduction window, these techniques may also be used in connection with other types of assays and other types of redox species.

Another embodiment of the present invention is a kit for conducting an assay. Preferably, such a kit includes one or more electrodes, probe sequences which are attached or can be attached to one of the electrodes, and an appropriate counterion reagent. Preferably, the counterion reagent will comprise ruthenium complexes. More preferably, the counterion reagent will comprise $Ru(NH_3)_5py^{3+}$ in a liquid solution. Additionally, a kit according to the present invention can include other reagents and/or devices which are useful in preparing or using any biological samples, electrodes, probe sequences, target sequences, liquid media, counterions, or detection apparatus, for various techniques described herein or already known in the art.

EXAMPLE 1

Synthesis of $Ru(NH_3)_5pyridine^{3+}$

Ruthenium pentaamine pyridine was synthesized as follows:

1. 0.2 g Chloropentaammineruthenium(III) dichloride (6.8× $10^{-4}$ M) was digested with 4 ml of a solution of silver trifluoroacetate. The resulting solution of chloro-pentaamine ruthenium trifluoroacetate was collected after filtration.

2. The ruthenium (III) complex was then reduced by zinc amalgam in the presence of 30-fold excess (about 1 g) of pyridine.

3. After 20 minutes reaction time, saturated ammonium hexafluorophosphate was added to the brilliant yellow reaction mixture to precipitate the yellow solid pentaamminepyridineruthenium (II) hexafluorophosphate, $[(NH_3)_5Ru(py)](PF_6)_3$.

4. The ruthenium complex was then recrystallized from methanol-water mixtures with some loss in yield.

5. A 0.030 g sample of $Ag_2O$ (0.00013 M) was dissolved in 1 ml of water with a minimum of trifluoroacetic acid. In this solution, a portion of 0.00025 M pentaamminepyridineruthenium (II) hexafluorophosphate was digested. The solution was then filtered to remove the resulting metallic silver. Several milliliters of saturated ammonium hexafluorophosphate were then added to yield the solid ruthenium (III) pentaamine pyridine which was collected by filtration and washed with cold ethanol.

EXAMPLE 2

Performing a Hybridization Assay Using $Ru(NH_3)_5py^{3+}$

A DNA hybridization assay in which $Ru(NH_3)_5py^{3+}$ is used as a counterion can be conducted as follows:

1. A DNA strand is identified as containing a sequence of interest. From this DNA strand, a single stranded oligonucleotide is isolated; this oligonucleotide is approximately 20 bp units in length and contains a sequence that is complementary to the sequence of interest. This oligonucleotide is then amplified by PCR to create probe strands.

2. A gold electrode is provided which contains a porous layer of avidin on its surface. Each probe strand is covalently coupled at one end to a biotin complex. The biotin complexes are then allowed to interact with the avidin on the electrode effectively immobilizing a plurality of probe strands on the electrode surface. Excess probe strands which did not adhere to the avidin layer on the electrode are then washed away using a liquid washing solution.

3. DNA to be interrogated for the sequence of interest is isolated from a tissue sample from a patient. PCR is used to create a plurality of target strands from the region of DNA suspected of containing the sequence of interest.

4. The plurality of target strands is then introduced to a liquid medium in contact with the immobilized probe strands. The quantity of target strands substantially exceeds the quantity of immobilized probe strands. The temperature, pH, and contents of the liquid medium are adjusted so as to allow a target strand to hybridize to an immobilized probe only if the target strand contains a sequence that is perfectly complementary to that of the probe.

5. After the target strands have interacted with immobilized probes, excess unbound target strands are washed away using a liquid washing solution.

6. A liquid solution containing $Ru(NH_3)_5py^{3+}$ ions is introduced to the electrode surface containing the immobilized nucleic acid strands.

7. An electrical potential is applied to the electrode. Current, corresponding to the reduction of trivalent ruthenium complexes to divalent, is measured at the electrode surface.

8. The amount of measured current is evaluated to determine whether it likely corresponds to single stranded or double stranded nucleic acid. This determination is used to conclude whether the DNA being interrogated contains the sequence of interest.

What is claimed is:

1. A method for detecting a polynucleotide, comprising the steps of:
   immobilizing a target polynucleotide on an electrode;
   contacting the target polynucleotide with a ruthenium complex of the formula:

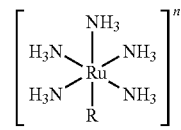

wherein R is an electron withdrawing ligand and n is an integer; and
   electrochemically detecting the ruthenium complex as an indicator of the presence of immobilized target polynucleotide;
   wherein no deaeration step is performed prior to electrochemically detecting the ruthenium complex.

2. The method of claim 1, wherein detecting comprises quantitating the target polynucleotide.

3. The method of claim 1, wherein the detecting step is performed in the presence of molecular oxygen.

4. A method for quantitating polynucleotide, comprising:
   binding polynucleotide to an electrode;
   contacting the polynucleotide with a ruthenium complex of the formula:

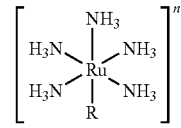

wherein R is an electron withdrawing ligand and n is an integer; and
   electrochemically detecting the quantity of ruthenium complex associated with the polynucleotide;
   wherein no deaeration step is performed prior to electrochemically detecting the quantity of ruthenium complex.

5. The method of claim 4, wherein the detecting step is performed in the presence of molecular oxygen.

6. The method of claim 5 wherein R is pyridine or a pyridine derivative and n is 3+ or 2+.

7. The method of claim 5 wherein the ruthenium complex is ruthenium (III) pentaamine pyridine.

8. The method of claim 5 wherein said electrochemically detecting comprises amperometry.

9. A method of detecting a polynucleotide, comprising:
   immobilizing a target polynucleotide on an electrode;
   contacting the target polynucleotide with a redox moiety; and
   electrochemically detecting the redox moiety as an indicator of the presence of immobilized target polynucleotide;
   wherein no deaeration step is performed prior to electrochemically detecting the redox moiety.

10. The method of claim 9 wherein the redox moiety comprises a transition metal.

11. The method of claim 9 wherein the redox moiety comprises ruthenium.

12. The method of claim 9 wherein the redox moiety comprises ruthenium and an electron withdrawing ligand.

13. The method of claim 12 wherein the electron withdrawing ligand is selected from the group consisting of: pyridine, a pyridine derivative, pyrimidine, pyridazine, pyrazine, a phosphite derivative, an isonitrile derivative, rutheniumpentaamine pyrazine, and polyvinyl pyridine.

14. The method of claim 9 wherein the redox moiety has a reduction potential at the electrode that is positive of −200 mV versus an Ag/AgCl reference.

15. The method of claim 9 wherein the redox moiety has a reduction potential at the electrode that is positive of −100 mV versus an Ag/AgCl reference.

16. The method of claim 9 wherein the redox moiety has a reduction potential at the electrode that is positive of 0 mV versus an Ag/AgCl reference.

17. The method of claim 9 wherein the redox moiety has a reduction potential at the electrode that is between −100 mV and +200 mV versus an Ag/AgCl reference.

18. A kit for detecting a polynucleotide, comprising:
an assay device having a binding portion capable of binding target polynucleotide; and
a counterion reagent able to associate with the target polynucleotide;
instructions for using said assay device for determining electrochemically whether any target polynucleotide is present, in which no deaeration step is performed prior to said determining.

19. The kit of claim 18 wherein the counterion reagent has the formula:

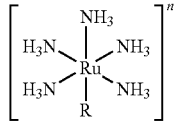

wherein R is an electron withdrawing ligand and n is an integer.

20. The kit of claim 19 wherein the electron withdrawing ligand is selected from the group consisting of: pyridine, a pyridine derivative, pyrimidine, pyridazine, pyrazine, a phosphite derivative, an isonitrile derivative, rutheniumpentaamine pyrazine, and polyvinyl pyridine.

21. The kit of claim 20 wherein R is pyridine.

22. A method of detecting a polynucleotide, comprising:
immobilizing a target polynucleotide on a non-gold electrode;
contacting the target polynucleotide with a redox moiety; and
electrochemically detecting the redox moiety as an indicator of the presence of immobilized target polynucleotide;
wherein no deaeration step is performed prior to electrochemically detecting the moiety.

23. The method of claim 22 wherein the non-gold electrode is a carbon electrode.

24. The method of claim 22 wherein the redox moiety is $Ru(NH_3)_6^{3+}$.

* * * * *

UNITED STATES PATENT AND TRADEMARK OFFICE
CERTIFICATE OF CORRECTION

| | | |
|---|---|---|
| PATENT NO. | : 7,615,348 B2 | Page 1 of 1 |
| APPLICATION NO. | : 11/836046 | |
| DATED | : November 10, 2009 | |
| INVENTOR(S) | : Donald M. Crothers et al. | |

It is certified that error appears in the above-identified patent and that said Letters Patent is hereby corrected as shown below:

Column 1, Line 48, change "hexaamine" to, --hexaammine--.

Column 3, Line 44, change "DRAWINGS" to, --DRAWING--.

Column 4, Line 5, change "hexaamine" to, --hexaammine--.

Column 4, Line 29, change "advantagous" to, --advantageous--.

Column 4, Line 34, change "pentaamine" to, --pentaammine--.

Column 4, Line 47, change "pentaamine" to, --pentaammine--.

Column 5, Line 31, change "Rutheniumpentaamine" to, --Rutheniumpentaammine--.

Column 5, Line 33, change "Rutheniumpentaamine" to, --Rutheniumpentaammine--.

Column 6, Line 3, change "pentaamine" to, --pentaammine--.

Column 6, Line 7, change "pentaamine" to, --pentaammine--.

Column 9, Line 4, change "Phophotriesters" to, --Phosphotriesters--.

Column 10, Line 42, change "pentaamine" to, --pentaammine--.

Column 10, Line 47, change "chloro-pentaamine" to, --chloro-pentaammine--.

Column 11, Line 1, change "pentaamine" to, --pentaammine--.

Column 12, Line 44, change "pentaamine" to, --pentaammine--.

Column 12, Line 66, change "rutheniumpentaamine" to, --rutheniumpentaammine--.

Column 14, Line 8, change "rutheniumpentaamine" to, --rutheniumpentaammine--.

Signed and Sealed this
Twenty-seventh Day of September, 2011

David J. Kappos
*Director of the United States Patent and Trademark Office*